United States Patent
Kuehnle et al.

(10) Patent No.: US 8,748,161 B2
(45) Date of Patent: Jun. 10, 2014

(54) EXTRACTION OF LIPID FROM MICROBIAL BIOMASS WITH HYDROPHOBIC IONIC LIQUID SOLVENT

(75) Inventors: Adelheid R. Kuehnle, Honolulu, HI (US); Norie Anne B. Nolasco, Waipahu, HI (US)

(73) Assignee: Kuehnle AgroSystems, Inc., Honolulu, HI (US)

( * ) Notice: Subject to any disclaimer, the term of this patent is extended or adjusted under 35 U.S.C. 154(b) by 0 days.

(21) Appl. No.: 12/954,141

(22) Filed: Nov. 24, 2010

(65) Prior Publication Data

US 2011/0124034 A1     May 26, 2011

Related U.S. Application Data

(60) Provisional application No. 61/264,533, filed on Nov. 25, 2009.

(51) Int. Cl.
*C12N 1/12*     (2006.01)

(52) U.S. Cl.
USPC .................................. 435/257.1; 435/243

(58) Field of Classification Search
CPC .................................. C11B 1/10; G01N 33/92
USPC ............................... 435/29, 267, 271; 426/61
See application file for complete search history.

(56) References Cited

U.S. PATENT DOCUMENTS

| | | | | |
|---|---|---|---|---|
| 5,711,983 A | * | 1/1998 | Kyle et al. | 426/635 |
| 6,166,231 A | * | 12/2000 | Hoeksema | 554/12 |
| 2007/0048848 A1 | * | 3/2007 | Sears | 435/134 |

FOREIGN PATENT DOCUMENTS

WO    WO 2009/017425    *   2/2009        C11B 7/00

OTHER PUBLICATIONS

Greaves and Drummond, Protic Ionic Liquids: Properties and Applications, 2008, Chem. Rev. 108: 206-237.*
Gutowski et al., Controlling the Aqueous Miscibility of Ionic Liquids: Aqueous Biphasic Systems of Water-Miscible Ionic Liquids and Water-Structuring Salts for Recycle, Metathesis, and Separations, 2003, J. Am. Chem. Soc. 125: 6632-6633.*
Freire et al., Ion specific effects on the mutual solubilities of water and hydrophobic ionic liquids, 2008, The Journal of Physical Chemistry B 113(1): 202-211.*

* cited by examiner

*Primary Examiner* — Jon P Weber
*Assistant Examiner* — Robert Yamasaki
(74) *Attorney, Agent, or Firm* — Saliwanchik, Lloyd & Eisenschenk

(57) ABSTRACT

The subject invention relates to novel methods for treating microbial biomass and uses thereof. In particular, this invention provides methods for production of lipids using hydrophobic ionic liquid solutions, and subsequent uses of biomass components in food, biofuels, and as chemical precursors. Further, this invention provides methods for recovering the ionic liquids using an antisolvent, thus enabling subsequent reuse of the ionic liquids.

30 Claims, No Drawings

EXTRACTION OF LIPID FROM MICROBIAL BIOMASS WITH HYDROPHOBIC IONIC LIQUID SOLVENT

CROSS-REFERENCE TO RELATED APPLICATION

The present application claims the benefit of U.S. Provisional Application Ser. No. 61/264,533, filed Nov. 25, 2009, which is hereby incorporated by reference herein in its entirety, including any figures, tables, or drawings.

ENRICHMENT OF PROCESS FEEDSTOCK

The present application acknowledges the research funding, in part, from the National Defense Center of Excellence for Research in Ocean Sciences (CEROS) Contract 57770 to Kuehnle AgroSystems, Inc. The government has certain rights in the invention.

FIELD OF THE INVENTION

The present invention pertains generally to methods for treating a microbial biomass to yield the preferred compositions and uses thereof.

BACKGROUND OF THE INVENTION

Microbial biomass has been utilized for various applications, such as sources of high energy-content fuels, human and/or animal food, and as chemical precursors. Their lipid components are being validated as renewable, sustainable sources of commodity chemical feedstocks. Other components, such as proteins and carbohydrates, can also serve as attractive resources for food supplements. For example, microbial proteins have been useful sources for protein supplements in rations for terrestrial and companion animals, and in diets for aquatic animals. In addition, microbial carbohydrates are excellent sources of industrial compounds as well as feedstock for fermentation systems.

Currently, organic solvents such as hexane are used to extract lipids from the biomass. One disadvantage is that this technique renders the remaining components unusable for further applications such as feed, fermentation or co-firing, unless additional processing such as steam stripping is used to remove the solvent. However, such additional processing has not been widely practiced in commercial production of microbial biomass, for example, for production of polyunsaturated fatty acids (PUFAs); rather, the delipidated biomass is discarded.

Another disadvantage for extraction of lipids using organic solvents is that the extracted lipids need to be further processed, otherwise they may be unusable for subsequent applications. For example, for use of hexane-extracted lipids for biofuels, the extract requires degumming and removal of pigments as well as significant hydrogenation to yield saturated lipids from the polyunsaturated hydrocarbons.

Therefore, a need exists in the field for technologies and methods, which are not only capable of effectively removing lipids from the biomass, but also retaining valuable residual compositions. Further, a need exists for methods that selectively remove lipids from the biomass, thereby avoiding additional processing steps associated with subsequent use of lipids such as for biofuels.

SUMMARY OF THE INVENTION

The subject invention provides a new method for treating a biomass, comprising: (a) applying hydrophobic ionic liquid (IL) solution to biomass so that a lipid-solvent phase is formed between IL and the desired fatty acids. Preferably, the desired fatty acids are saturated, or saturated and monounsaturated; and (b) removing said lipid-solvent phase, yielding a microbial biomass suitable for a myriad of applications without residual contamination by toxic organic solvents.

In certain embodiments, the treatment comprises: applying a solvent such as hydrophobic ionic liquid solution to the biomass so that a solvent mixture is formed; disturbing the solvent mixture under mild conditions to facilitate the formation of a saturated lipid-solvent phase; and removing the formed saturated lipid-solvent phase. As a result of such treatment, feedstock that is selectively delipidated for saturated, saturated and monounsaturated fatty acids, triglycerides, or other lipids can be obtained. Delipidation can be partial. In one embodiment, the resulting feedstock contains proteins and carbohydrates, which can be further enriched by one or more PUFAs.

In another embodiment, the feedstock may be suitable for further separation of various components or used as a whole meal. In another embodiment, the saturated, and saturated and monounsaturated lipid fraction can be further processed for biofuel applications or as a source of hydrocarbon compounds and reactive groups.

An additional embodiment of the invention provides a novel addition of a solvent to microbial biomass. Preferably, the solvent is non-toxic and non-volatile.

In another embodiment, lipids can be separated from the biomass using solvents in the absence of denaturing high temperatures. Although high temperature may accelerate the separation of the saturated lipids, it can damage the structure and function of many extractable components.

In a further embodiment, the solvent can be of a class of compounds comprising ionic liquids. In certain embodiments, the ionic liquids are specifically chosen for their chemical and physical properties, to thereby extract only those molecules of interest. Preferably, the solvent is reusable. Similar to the organic solvents, the solvent can be further recovered by distillation or other similar methods.

This invention further provides methods for recovering ionic liquids from the lipid-solvent mixture with the use of an antisolvent. The antisolvent is an inorganic salt solution, capable of binding IL to form an IL-salt mixture; thus it separates IL from the lipid-solvent mixture and further yields a lipid layer without contaminating IL residues. Salt from the IL-salt mixture can be further separated by addition of deionized water or any polar solvent; thus, IL can be recovered for subsequent reuse.

In one embodiment, the antisolvent can be any inorganic salt. Further, such inorganic salt is not only capable of removing the solvent, but also being recovered from the solvent by using deionized water or other compatible polar solvents.

This invention further provides a novel method for isolating the preferred lipid components.

In one embodiment, the invention provides a practical method for screening potential lipid-producing microbial classes, comprising: (a) determining total lipid content of potential lipid-producing algae using ionic liquids as a lipid extractant; and determining lipid content using fluorescence measurements.

In another embodiment, the preferred lipid components can be extracted from biomass, while the delipidated components remain suitable for consumption, for example, by retaining the activity and yields of proteins.

Other embodiments of the invention relate to the novel methods for lipid extraction that the biomass need not be dried prior to extraction, or can be extracted at relatively low temperatures.

Another embodiment of the invention relates to a practical, quick and direct method for screening potential lipid-producing algae strains by determining total lipid content of algae samples using fluorescence measurements.

In various embodiments, the subject invention has unique applications in bioprocess algae. The concentrated algae biomass can be treated for the removal of preferred fatty acids, while still capable of retaining viability of the remaining feedstock.

DETAILED DESCRIPTION

The subject invention relates to novel methods for treating microbial biomass and uses thereof. In particular, this invention provides methods for production of lipids using ionic liquid solutions, and subsequent uses of biomass components in food, biofuels, and as chemical precursors. Further, this invention provides methods for recovering the ionic liquids using an antisolvent, thus enables subsequent reuse of the ionic liquids. In addition, this invention provides practical methods for determining the lipid content of a biomass and screening potential lipid-producing microbial classes.

Definitions

Unless defined otherwise, all technical and scientific terms used herein have the meaning commonly understood by a person skilled in the art to which this invention belongs. As used herein, the following terms have the meanings ascribed to them unless specified otherwise.

The articles "a" and "an" are used herein to refer to one or to more than one (i.e., to at least one) of the grammatical object of the article. By way of example, "an element" means one element or more than one element.

The term "culturing," as used herein refers to incubating a cell or organism under conditions wherein the cell or organism can carry out some, if not all, biological processes. For example, a cell that is cultured may be growing or reproducing, or it may be non-viable but still capable of carrying out biological and/or biochemical processes such as replication, transcription, translation, etc.

The term "biomass," as used herein refers to a mass of living or biological material and includes both natural and processed, as well as natural organic materials more broadly.

I. Microbial Biomass Composition and Uses.

Microbial biomass comprises lipids including essential fatty acids, high crude protein ingredients and carbohydrates, required for quality growth and thus useful in formulas for aquatic and terrestrial animal diets.

Microbial lipids include saturated or monounsaturated lipids, useful for production of biofuels. Similar to vegetable oils, these lipids can be processed into liquid transportation fuels such as biodiesel or jet fuel. In particular, certain microbes such as algae have much higher lipid yields per unit area than other oil crops, making them an attractive feedstock for use in commodity fuels.

The saturated lipids of microbial biomass can be further processed as a source of saturated hydrocarbon compounds for industrial applications. Preferably, saturated lipids contain saturated hydrocarbons of C10, C12, C14, C16, C17, or C18. Saturated lipids can further contain C20, C22, or C24 fatty acid components.

In addition, microbial lipids, PUFAs in particular, have been recognized for their high nutritional value. Therefore, they have been used in infant and adult food, pharmaceutical compositions, and nutritional supplements. Preferably, PUFAs are C18, C20 or C22 fatty acids (e.g., omega-6 or omega-3 fatty acids). These unsaturated lipids include docosahexaenoic acid (DHA, an omega-3), obtained from sources such as from algae or fungi, commonly the dinoflagellate *Crypthccodinium* or the fungus *Thraustochytrium*; alpha-linolenic acid (ALA, an omega-3); arachidonic acid (ARA, an omega-6); eicosapentaenoic acid (EPA, an omega-3); and gamma-linolenic acid and dihomo-gamma-linolenic acid (GLA and DGLA, respectively, each an omega-6).

Alternatively, microbial lipids can serve as a source of structured lipids for food, nutritional supplements, and medicines. These designer triacylglycerides, composed of fatty acids, are amenable to selective extraction and enrichment, as described in Osborn H T and Akoh C C *Comprehensive reviews in food sciences and food safety*, vol. 1: 93-103; 2002 and incorporated by reference herein. Structured lipids also include components such as ricinoleic acid, or Oleic acid (C18:1), which is a common monounsaturate in some algae oils and a direct precursor to ricinoleic acid in plant biosynthesis.

Production of microbial PUFA oils is known in the art. Extraction of PUFAs-containing oils from microbial sources is described in WO-A-97/36996 and WO-A-97/3703, and practiced for example in WO-A-92/12711 by using hexane. Use of other various organic solvents such as hexane, isopropanol, and supercritical carbon dioxide is known. Commonly, hexane is employed for extraction.

However, presence of PUFAs in biodiesel generally reduces its oxidative stability and makes the oil more susceptible to chemical degradation. Therefore, polyunsaturated oils are considered poor fuel oils. Accordingly, it is advantageous to use concentrated levels of saturated fatty acids in oil preparations.

Further, the delipidated microbial biomass contains valuable components such as proteins and carbohydrates. Proteins from microbial biomass can serve as a source for growth hormone peptides, disease resistance compounds, vaccines, and therapeutic proteins (D. Kyle, 2004, Application Number EP20020725276; "Delivery of disease control in aquaculture and agriculture using microbes containing bioactive proteins;" and references therein). In addition, similar to soybean proteins, proteins from microbial biomass can serve as promising sources for various industrial applications. Therefore, in the lipid extraction process, it is highly valuable to develop methods capable of recovering proteins intact or preserving their biological activity.

II. Biomass Processing Using Ionic Liquids.

Ionic liquids are salts composed of bulky organic cations and small inorganic anions, with melting points below ambient temperatures. They are non-volatile, non-explosive, environmental friendly, and easy to prepare. In addition, ionic liquids can be made immiscible with organic solvents or water, and recovered for subsequent reuse.

The chemical and physical properties of ionic liquids are 'tunable' by a combination of anion and cation; thus, ionic liquids can be designed to extract only those molecules of interest. By varying its ionic structure, characteristics of ionic liquids including viscosity, hydrophobicity, and hydrogen-bonding capability can be further modified to achieve the desired solvent properties. Consequently, by using ionic liquids, a more complete separation of lipids from the biomass can be achieved without requiring denaturing high temperatures (Brennecke and Maginn, 2001). In addition, use of ionic liquids increases rates of lipid soluabilization, thus is attractive for streamlined industrial processing. Researches have shown that ionic liquids can serve as a replacement for the toxic organic solvents used in liquid-liquid extractions for component separations (reviewed in Davis and Fox, 2003).

Further, the increased selectivity in extraction processes can facilitate the occurrence of certain reactions such as isomerizations, hydrogenation, aldol and benzoin condensations, organometallic, 1,3-dipolar additions, and Friedel-Crafts alkylation and acylation reactions, which can be important for the generation of desired end products. Use of ionic liquids for catalysis has been detailed in several extensive reviews (e.g., Olivier-Bourbigou and Magna 2002), whereby the ionic liquids can act as both a catalyst and a solvent. The production of desired reaction products can be further facilitated by addition of enzymes produced by genetic engineering of organisms into the ionic liquids. For example, adding the enzyme cellulase in an ionic liquid reaction medium facilitates the conversion of cellulose to glucose and cellobiose.

There are a variety of ionic liquids. Structural electronic (computer based) modeling can be used to identify the suitable ionic liquids for extraction of particular lipids. For reasons described above (see Supplement to Chimica Oggi/ CHEMISTRY TODAY•Vol 25 nr 6•Green Chemistry/Ionic liquids; 2007), characteristics of protic ionic liquids are applicable to industrial scale-up. Examples of protic ionic liquids are described, for example, in *Chem. Rev.* 108: 206-237 (2008), the contents of which are hereby incorporated by reference.

This invention overcomes a principal barrier of using the process feedstock, that is, the ability to find a solvent that selectively separates the desired lipids from the biomass, without requiring the use of toxic organic solvents or high temperatures that would denature the remaining components.

Due to the cost and logistics associated with the handling and transporting biomass from farm to refinery and to feed manufacturers, it is preferable that lipid and protein meal components can be separated on site by the algae farmer thus revenues from the biomass can be maximized. It is further preferable to develop a substitute for existing solvents that are toxic, explosive, flammable, and carcinogenic, thereby avoiding additional facility management cost incurred for removing the solvents.

Partial or complete cell disruption is required for extraction of cellular components. It is known in the art that solvents such as methanol can disrupt cells, thus allowing dyes to penetrate cells and further localize, bind, and interact with lipids. Further, such solvents could act as co-solvents in the presence of hydrophilic agents to effect lipid extraction by lipid coalescence for phase separation.

In one embodiment, non-toxic solvents are applied to biomass from photosynthetic, heterotrophic, or any other bioprocess microbes for selective delipidation. In another embodiment, non-toxic solvents are applied for yielding protein products, suitable for terrestrial or aquatic animal feed together with residual lipid and carbohydrate components. In another embodiment, the resulting proteins are suitable as bioactive compounds, meal components, or as purified products for industrial applications. In further embodiments, non-toxic solvents are applied for the selective removal of structured lipids. In still further embodiments, non-toxic solvents are applied to the biomass, yielding components useful in fuels and fuel refining, or as catalytic co-products such as, for example, butadiene, acrylamide, polyols and epoxides.

This invention further embodies unique applications in microbes such as algae. Algae have become a highly desirable source for feed components. This is largely due to a continuous increasing in price of traditional food sources such as soybean and fish.

In this invention, algae selected primarily for their ability to provide proteinaceous meal or bioactive proteins, and secondarily for their ability to provide PUFAs, can also advantageously be used for their high lipid content as a source for saturated lipids. The invention further generates a variety of lipids, including PUFAs which can be used as meal, and the remaining saturates, or saturates and monounsaturates for further applications. Depending on the algae strain, the meal containing algae lipids thus becomes enriched in PUFAs.

In certain embodiments, species of *Chlorella* that may have 70% of its total FAME yield be polyunsaturates are now near 100% polyunsaturates in the processed meal; and species of *Tetraselmis*, that may have only 20% of its total FAME yield be polyunsaturates are now greater than 85% and preferably near 100% polyunsaturates. For yet another algae, *Nannochloropsis* spp., the fatty acid composition can be equally split such that saturates comprise 42%, monounsaturates comprise 29% and PUFAs comprise 25%. In this case, a reasonable yield of biofuel hydrocarbons is realized, with PUFAs still present for concentrating in the treated feedstock slurry.

Further, algae with sufficiently high lipid content are preferred for the design and execution of feedstock production. A continued need exists for such high-lipid strains due to the revived interest in algae biomass as feedstock for biofuels, and new uses such as natural oil polyols and derivatized hydrocarbons (Y. Christi., "Biodiesel from microalgae," *Biotechnology Advances* 25:294-306; 2007).

In addition, proper selection of the microbe strains grown for biomass production can be used to maximize revenues. Thus, the subject invention further relates to a novel, practical, easy and quick method for selecting desired microbial strains, comprising: sonicating a sample of potential microbe strain with ionic liquids; and determining the lipid content using fluorescence measurements.

Algae Culture Techniques

In various embodiments, freshwater, brine, and marine algae can be cultured in a variety of media and environmental conditions as are known to those skilled in the art (Andersen, R. A.; "Algal Culturing Techniques," Phycological Society of America, Elsevier Academic Press; 2005). Some algae can further be cultivated in more than one medium conditions, including in both freshwater and in saltwater. In an embodiment, marine algae may be grown in medium containing about 1 M NaCl. In other embodiments, marine algae may be grown in medium containing NaCl at a concentration from 0.1 M up to 4.0 M. In another embodiment, marine algae may be grown in seawater.

Culture temperatures may be at ambient temperature (20-25° C.), or may be at 25 to 29° C. In some embodiments, the cultivation temperatures may reach 35° C. or even as high as 42° C. for limited time periods during the daily cycle. In some embodiments in which the algae are heterotrophic or mixotrophic, algae culture supplemented with energy sources such as glucose or whey can be grown under darkness.

In some embodiments, photoautotrophic or mixotrophic algae can be cultured under illumination with bright white and warm fluorescent lights (for example, about 30 to 200 micromol/m$^2$/sec or even to 400 micromol/m$^2$/sec) with, for example, about a 12 hour light:12 hour dark photoperiod or a 14 hour light:10 hour dark photoperiod or a 16 hour light:8 hour dark period, or even a 24 hour light period. In some embodiments, algae can be cultured under natural illumination, with or without supplemental shading in photo bioreactors, in covered (closed) culture systems, or in open culture systems such as in raceways and ponds.

In another embodiment, algae can be cultured on substrates that facilitate the algal proliferation without disturbing the medium.

Algae can be cultured in a variety of growth medium. In one embodiment, algae can also be cultured on solidified medium such as by 20 g/L agar, or embedded in solidified medium such as in alginate or other types of matrix including mesh. In some embodiments for liquid culture, the volume is between about 25 mL to 1000 mL. In other embodiments, it can be between about 1 L to about 100 L. In some embodiments, the volume is between about 1 L to about 10 L. In some embodiments, the volume is about 6 L. In some embodiments in outdoor culture, volumes are generally about 100 to 600 L, or in larger increments to about 1200 L, 2400 L, and up to about 20,000 L, for example, in bioreactors, including enclosed or covered ponds. In other embodiments, the culture is in 50,000 L raceways or ponds. In yet other embodiments, the culture is in expansive ponds, including in polyculture, of about 1 to 10 acres each.

In various embodiments, cells of *Tetrasclmis, Nannochloropsis*, or other green algae, can be grown in, for example, f/2 medium. F/2 medium is composed of seawater with $8.83\times10^{-4}$ M $NaNO_3$, $3.63\times10^{-5}$ M $NaH_2PO_4.H_2O$, $1.07\times10^{-4}$ M $Na_2SiO3.9H_2O$ (included for diatoms), with trace metal ($1\times10^{-5}$ M $FeCl_3.6H_2O$, $1\times10^{-5}$ M $Na2EDTA.2H_2O$, $4\times10^{-8}$ M $CuSO_4.5H_2O$, $3\times10^{-8}$ M $Na_2MoO_4.2H_2O$, $8\times10^{-8}$ M $ZnSO_4.7H_2O$, $5\times10^{-8}$ M $CoCl_2.6H_2O$, and $9\times10^{-7}$ M $MnCl_2.4H_2O$); and vitamins ($1\times10^{-10}$ M Vitamin B12, (cyanocobalamin), $2\times10^{-9}$ M biotin, and $3\times10^{-7}$ M thiamine. HCl). *Nitzschia* can also be grown in one of several media such as G/2 medium (GPM medium, as described by A. R. Loeblich III, "A seawater medium for dinoflagellates and the nutrition of Cachonina niei," *Journal of Phycology* 11: 80-86; 1975).

In some embodiments, algal cells can be collected in the early, middle, or late logarithmic phase of growth, or even the stationary phase of growth, by centrifugation. The cell pellet can be washed to remove cell surface materials, which may cause clumping of cells. Lugol's staining, as is known in the art, is used for cell counts using a hemacytometer. Alternatively, flow cytometry or spectrophotometry can be used given an appropriate standard curve.

Cryopreservation of Strains

Cryopreservation is employed in various embodiments to preserve the genotype of the organisms of interest. Algae strains are cryopreserved in various cryoprotective agents as is known in the art. In some embodiments, this may be in 7% DMSO, 7% MeOH, 20% glycerol, or in the culture medium itself Various freezing methods may be employed. In one embodiment, this is practiced by direct immersion of cryovials into a Dewar with liquid nitrogen after the addition of cryoprotective agents. In another embodiment, this is practiced by slow cooling to −50° C. using "Mr. Frosty," which controls cooling at −1° C./min, with the addition of isopropanol. Cells can be thawed by various means. In an embodiment, cells are thawed by placing the frozen cryovials into a 35° C. water bath for several minutes. Cells in the vials are then allowed to settle, or are centrifuged at 500×g for 5 minutes. Without disturbing the pellet, the supernatant is decanted and fresh culture medium is added.

Cultured Biomass

A variety of different microbes can be used for this invention. For example, numerous algae strains have been recognized for their valuable compositions, useful for a variety of applications. In some embodiments, algae are selected from the group consisting of *Amphora, Anabaena, Anikstrodesmis, Botryococcus, Chaetoceros, Chlorclla, Chlorococcum, Cyclotella, Cylindrotheca, Euglena, Hematococcus, Isochrysis, Monodus, Monoraphidium, Nannochloris, Nannochloropsis, Navicula, Nephrochloris, Nephroselmis, Nitzschia, Nodularia, Nostoc, Oochromonas, Oocystis, Oscillartoria, Parachlorella, Pavlova, Phaeodactylum, Pinguiococcus, Playtomonas, Pleurochrysis, Porphyra, Pseudoanabaena, Pyramimonas, Rhodomonas, Selenastrum, Scenedesmus, Stichococcus, Synechococcus, Tetraselmis, Thalassiosira*, and *Trichodesmium*.

In other embodiments, algae can be commercially cultivated. *Chlorella* spp. are of interest due to their ease of use in large-scale cultivation and high nutrient contents (proteins, carbohydrates, vitamins, other biologicals). *Chlorella* has been commercially cultivated as a promising source of primary food, health food or food supplement. It has also been used in cosmetics, carbon sequestration and waste water treatment. Heterotrophically grown *Chlorella* has a higher total lipid content (55% of total dry weight) compared to autotrophically grown algae (15%) (Xu, H., Miao, X., and Wu, Q. J. of Biotechnology 126: 499-507; 2006). *Chlorella*, as well as *Tetraselmis* and *Nannochloropsis* spp., are popular as whole cells for feed to fish fingerlings or rotifers due to high nutrient contents. They are promising for carbon sequestration in large-scale cultivation as well.

In some embodiments, *Nitzschia* species are of interest not only because of concurrent presence of C20:4 (AA), C20:5 (EPA), and C22:6 (DHA) in the biomass, and but also their ability to be cultivated heterotrophically, phototrophically, and mixotrophically (Wen, Z. Y. & Chen. F. "Production potential of eicosapentaenoic acid by the diatom *Nitzschia lacvis*." *Biotechnology Letters* 22: 727-733; 2000). In other embodiments, algae strains used have been mutated, mutagenized, or genetically engineered.

Harvested Biomass

Algae are commonly cultured in liquid suspension, and will autoflocculate by stirring and subsequent suspension of the culture medium. Separation of the cultivated algae from the culture medium is required for subsequent processing of the algal biomass. Many means for separation are known in the art, such as use of floating suction dredgers and thickening drums or filters.

Microalgae can be harvested by: first, separating majority of water from the algae-salt water slurry; second, further separating the algae from the algae-salt water slurry by techniques such as by gravitation, centrifugation, filtration including tangential flow filtration, or flocculation effected by increasing the pH of the algae-salt water slurry. In one embodiment, the wet biomass is used as a concentrated slurry. In other embodiments, the algae concentrate is dried to a desired degree of moisture level, using means known in the art such as oven drying, spray drying, drum drying, and sun drying. Freeze-drying (lyophilization) is useful for analysis of smaller sample sizes. Freeze-dried samples are preferentially stored at −80° C. under $N_2$ to prevent oxidation of PUFAs.

Cells can be disrupted by osmotic or mechanical shock. For example, for smaller scale preparations, cells can be disrupted by ultrasonic agitation. For larger preparations, cells can be disrupted by agitation in bead mills and high-pressure homogenizers. In an embodiment, cells are disrupted by exposure to minimal amount of solvents such as alcohols including methanol, acetone, or DMSO. Other means for harvesting and disrupting the cells are described (E. Molina Grima, E.-H. Belarbi, F. G. Acien Fernandez, A. Robles Medina, Yusuf Chisti. 2003. "Recovery of microalgal biomass and metabolites: Process options and economics," *Biotechnology Advances* 20: 491-515) and incorporated by reference herein.

Compositional Analysis.

Crude lipids can be extracted from harvested biomass proceeds through several methods, such as mechanical pressing with expellers, use of organic solvents such as hexane, benzene or ether, and use of supercritical fluids and enzymes. In one embodiment, 95% lipid extraction is achieved using combined methods of hexane solvent extraction and expeller methods. In another embodiment, 100% lipid extraction is achieved using supercritical fluid/$CO_2$ extraction.

Crude lipids extracted from harvested biomass may be further processed. In one embodiment, esterification is performed to allow analysis by gas chromatography of fatty acid methyl esters, as is well-known to those skilled in the art. In another embodiment, lipids are hydrolyzed (saponified). In another embodiment, saponification or esterification can be applied either concurrent with, or subsequent to, the actual lipid extraction from the biomass.

Proteins extracted from harvested biomass can also be further processed. For bioactive proteins, the protein conformation should be preserved during processing. Nutritional quality of proteins used for feed is determined based on the content, proportion, and availability of amino acids. Analysis of free amino acids can be processed by high performance liquid chromatography, as is known in the art.

Cell lipid content is also analyzed by fluorescence spectroscopy using fluorochromes such as Nile Red, BODIPY, Rhodamine B, which are applicable for lipids. In one instance, in the Nile Red assay, 0.04 mL of a Nile Red solution (0.1 mg/mL in acetone) is added to a fixed volume of a diluted algal culture (4 mL), and fluorescence is measured after 5 min using a spectrofluorimeter with the appropriate excitation and emission filters. Lipid content is calculated based on a standard curve. Standard curve is generated as is known in the art for fluorescence analysis. Lipid yield is determined by first measuring the weight (gravimetric), and then calculating extraction yield according to the following formula:

$$Y = \frac{m_e/m_t}{m_l/m_t} = \frac{x_{el}}{x_{tl}},$$

where $m_e$ is the mass of extracted lipids (g), $m_t$ is the prepared algae weight (g), $m_l$ is the total lipid mass of the algae preparation (g), $x_{el}$ is the extracted lipid fraction, and $x_{tl}$ is the total lipid fraction of the algae. Proteins are expected to partition substantially to the aqueous phase.

The invention will now be described, by way of example, with reference to the following Examples. Representative classes are the Eustigmatophyceae, Prasinophyceae, Bacillariophyceae, and the Chlorophyceae. These are provided merely for means of illustration, and are not to be construed as being limiting on the invention.

Example 1

Preparation of *Nannochloropsis* (Class Eustigmatophyceae) Biomass

Various *Nannochloropsis* algae (some have been also classified as Nannochloris) can be prepared. In one embodiment, a strain of *Nannochloropsis*, capable of retaining its lipid profile in nitrogen-deplete conditions under saturating irradiance is prepared. For cultivation, sterilized (121° C., 20 min) f/2 medium (lacking Si) is inoculated with 10% v/v inocula in log phase or in early stationary phase. Cells are initially cultivated in 600 ml f/2-Si medium in 1 L flasks at ambient temperatures (28 to 33° C.) with continuous shaking at 85 to 95 rpm (VWR shaker model OS500, dial setting 3). Cells are cultivated under 14 hours light/10 hours dark. Illumination intensity is 120 micromol/$m^2$/sec. Further cultivation is performed using a 1:10 dilution in 9-liter Pyrex carboys containing 6 L f/2 medium. The carboys are incubated at ambient temperature (28 to 33° C.) under a 14 hours light/10 hours dark light cycle with an intensity of 190 micromol/$m^2$/sec and constant air bubbling (Panther pump model Compact 106, <1.5 L/min). Cells are harvested after two weeks at a density of about 13.5 million cells/mL.

Standard techniques of gas chromatography are employed for fatty acid methyl esters (FAMES) analysis. Under the culture conditions of the *Nannochloropsis*. of this Example, the profile of saturates C14:0 up to C24:0 is about 42% saturates of total FAMES detected, the bulk (35%) being C16:0. The profile of monounsaturates C16:1 up to C24:1 is about 29% monounsaturates of total FAMEs detected, the bulk (23%) being C16:1. The profile of polyunsaturates C16:2,3,4, C18:2, C18:3, C20:2, C20:3, C20:4 (AA), C20:5n-3 (EPA), C22:5, and C22:6n-3 (DHA) is about 25% polyunsaturates of total FAMES detected, the bulk (17% of FAMEs) being EPA. The ratio of monounsaturates to polyunsaturates is 1:1. In general, the total fatty acid methyl esters comprise 24% to 26% of the dry weight of biomass.

For this strain, FAME composition can vary, as manifested in the ratio of monosaturates to polyunsaturates. Thus, while the percentage of saturates remains constant (at 42-43%), the ratio of monosaturates to polyunsaturates can increase to, for example, 2.5:1 (41% monounsaturates: 16.5% polyunsaturates).

Example 2

Preparation of *Tetraselmis* (Class Prasinophyceae) Biomass

An isolate of *Tetraselmis* spp CCMP963, a Tahitian *Tetraselmis*, is obtained courtesy of Oceanic Institute (Waimanalo, Hi.) and cultured as described in Example 1. After two weeks, the harvested culture density is 11.4 million cells/mL. The GC profile of saturates C14:0 up to C24:0 is about 10% saturates of total FAMEs detected, and comprises largely (8.7%) of C16:0. Monounsaturates are 70% of total FAMEs detected, and comprise largely (70%) of C18:1. Polyunsaturates are 20% of total FAMEs detected, and comprise largely (17%) of C18:2. The ratio of monosaturates to polyunsaturates is 3.5:1. Total fatty acid methyl esters comprise 38% of the dry weight of biomass.

Example 3

Preparation of *Nitzschia frustulum* (Class Bacillariophyceae—Pennales) Biomass

This diatom is exemplified by NREL NITZ S44. It is grown in 1/3 Soil+Seawater Medium composed of 1 part seawater containing soil extract with two parts tap water (http://web.biosci.utexas.edu/utex/mediaDetail.aspx?mediaID=11). The GC profile of saturates C 14:0 up to C24:0 is about 28% saturates of total FAMEs detected, and comprises largely (24%) of C16:0. Monounsaturates are 46% of total FAMEs detected, and comprise largely (43%) of C 16:1. Polyunsaturates are 26% of total FAMEs detected, including 1.5% DHA, 7% EPA and 6% ARA. Total fatty acid methyl esters comprise 22% of total biomass.

Example 4

Preparation of *Chlorella protothecoides* (Class Chlorophyceae) Biomass

*Chlorella* cells, cryopreserved in culture medium without adding cryoprotective agents and directly submerged in liquid nitrogen, are thawed and used to inoculate sterilized (121 C, 20 min) liquid medium. This species is valuable due to its ability to produce high lipid content (55%) under darkness in medium supplemented with glucose. Typical heterotrophic medium for *C. protothecoides* comprises 0.3 g/L $K_2HPO_4$, 0.7 g/L $KH_2PO_4$, 0.3 g/L $MgSO_4.7H_2O$, 0.003 g/L $FeSO_4.7H_2O$, 0.0125 g/L NaCl, 0.015 g/L $CaCl_2$, $1\times10^{-5}$ g/L thiamine.HCl, glucose 10 g/L Bacto peptone 0.5 g/L (or 0.1 g/L glycine), and 1 ml Arnon's solution (2.9 g/L $H_3BO_3$, 1.8 g/L $MnCl_2.H_2O$, 0.22 $ZnSO_4.7H_2O$, 0.08 g/L $CuSO_4.5H_2O$, 0/018 g/L $MoO_3$). Heterotrophic cultivation of *C. protothecoides* is initially performed in a 500-ml Erlenmeyer flask containing 250 ml medium at 22° C. (or at higher ambient temperature) under continuous shaking at about 180 rpm in the dark. Further heterotrophic cultivation is performed with 1:10 dilution in an 8-liter carboy containing 6 L medium. The carboy is incubated under darkness at relatively high ambient temperature (28° C. to 33° C.) with constant air bubbling. Cells are harvested after 13 days (about 17.6 million cells/mL) or until a desired density and/or growth stage is attained.

This *Chlorella*, grown under the conditions described above, yields a GC profile of saturates C14:0 up to C24:0 at about 31% saturates of total FAMEs detected, and comprises largely (30%) of C 16:0 and C 17:0 (margaric acid). Monounsaturates are 4% of total FAMEs detected, and comprise largely (3%) of C18:1. Polyunsaturates are 53% of total FAMEs detected, comprise largely (46%) of C18:3 (ALA). Total fatty acid methyl esters comprise 8% of total biomass. Under these conditions, this *Chlorella* performs similar to phototrophic *Chlorella* spp., such as NREL CHLOR01, with the principal distribution of FAMEs among C16:0 and C18:3. This is with 4% FAMEs yield of biomass (about 31% of the total lipids). This latter *Chlorella* is cultivated, for example, in Bristol's freshwater medium with 0.25 g/L $NaNO_3$ (2.94 mM), 0.025 g/1 $CaCl_2.2H_2O$ (0.17 mM), 0.075 g/L $MgSO_4.7H_2O$ (0.3 mM), 0.075 g/L $KH_2PO_4$ (1.29 mM), 0.35 g/L $K_2HPO_4$ (0.43 mM), 0.025 g/L NaCl (0.43 mM), 1.0 g/L Difco Bacto proteose peptone, pH 6.8.

Example 5

Preparation of Green Coccoid Chlorophyte Biomass

Green coccoid chlorophyte is a unicellular alga that can be grown in sterilized f/2 medium as described in Example 1. Alternatively, it can be grown in freshwater, or freshwater medium such as TAP with acetate used for *Chlamydomonas*. The profile of saturates C 12:0 up to C22:0 is about 28% saturates of total FAMEs detected, with the dominant class being C16:0 (21%). Monounsaturates are 8% of total FAMEs detected. Polyunsaturates are 65% of total FAMEs detected, with the dominant class being C16:2,3,4 (18%), C18:2 (16%), and C18:3 (30%). Total fatty acid methyl esters comprise up to 13% of biomass, and 87% of total lipid content (about 16% of total biomass). When grown in seawater medium, this species shows negligible changes in lipid content under nitrogen-depletion with saturating irradiance levels. However, in freshwater medium, cell lipid content increases under nitrogen-depletion with saturating irradiance.

Example 6

Extraction of Lipids from Biomass and Separation of Lipids from the Remaining Protein Components Cell biomass is prepared as described in previous Examples. For example, cells are dried using a lyophilizer to maintain protein quality. In another example, cells are retained as concentrates following initial dewatering by means including tangential flow filtration (such as Millipore Pellicon 0.45 um filter cassette system) and centrifugation. Cultures with different percentage of algae contents such as 20, 80 or >90% algae can also be used. The slurry is then mixed with ionic liquids identified by computer modeling, which selects specific ionic liquids according to their molecular affinity with lipids. The preparation is then spun at a low speed (about 3000 rpm, preferably <5000 rpm), separating the hydrophobic lipids into a top layer and cellular debris into a pellet.

In one instance, a 1 L algae sample with cell density of $5\times10^{\wedge}8$ g/ml contains for example 0.1511 g of lipid (dry weight). In another instance, to obtain a minimum of 20 ug detectable total lipid, 1.27 mL of the algae sample is mixed with ionic liquids in a ratio of 3:1 v/v (algae:IL). In yet another instance, 300 ml of algae sample is further concentrated to a slurry of cell density of $4\times10^{\wedge}10$. This is frozen prior to lyophilization. The lyophilized sample is mixed with IL in a beaker, stirred with magnetic bar for 1 minute and sonicated using a sonicatior probe under an ice-bath at 45-47 C for 10 minutes and 55% amplitude. The sonicated mixture is centrifuged to allow complete separation of oil extract layer from biomass. The supernatant is withdrawn and tested for the presence of oil by Nile Red Assay as known the art and the pellet is lyophilized for further fatty acid quantitative analyses. The preparation is then mixed for example by intermittent sonication for 1 hour, with vortexing every 10 minutes for thorough mixing. The preparation is allowed to settle for the top layer to form. To facilitate faster formation of top layers, the mixture can be further centrifuged. The top layer is then separated from the mixture, and is prepared as is known in the art for quantitative analysis by gas chromatography or composition analysis HPLC; the pellet is stored for analysis, if necessary.

Example 7

Protein Analysis

The protein fraction is analyzed in various ways. First, proteins are precipitated with $(NH4)_2SO_4$ at 50% (w/v) saturation, and quantified by the Bradford method using adsorption measurements at 595 nm. Using this method, amino acid composition recovered from the resulting biomass can be determined. Second, stability of a representative protein is analyzed using actin, a 42 kDa protein known as G-actin in its monomeric form. Actin antibodies are commercially available (Actin Ab-5, BD Biosciences).

Protein purity is determined by visual inspection of Coomassie stained gels. Identity and antigenicity of recovered protein is determined by first electrophoretic separation, and then immunogenic Western blot analysis using standard protocols from the manufacturer. If the Western blot is proved to be unsuccessful, enzyme-linked immunosorbant assay can also be employed. Thus, even in the absence of molecular weight confirmation, protein recovery can still be determined based on immunogenic response.

Proteins can also be purified using ion exchange chromatography as is known in the art. The percentage of protein recovery is calculated by comparing the total protein recovered from the delipidated sample/non-delipidated sample× 100 for dried and for partially hydrated samples in duplicate. In one embodiment, stability, identity and antigenicity of G-actin protein are determined based on its molecular mass of 42 kDa.

In another embodiment, protein is extracted from the algal biomass obtained after IL extraction using a modified standard method for algae (Rausch. 1981. "The estimation of micro-algal protein content and its meaning to the evaluation of algal biomass I. Comparison of methods for extracting protein." Hydrobiologia 78, 237-251, incorporated herein by reference in its entirety) and analyzed using Bradford assay. Protein extraction was carried out by adding 3 mL of 0.5N NaOH to about 100 mg of dried biomass. The mixture was continuously stirred in a water bath for 10 minutes at 80° C. and the tubes quickly cooled to room temperature under cold running water. The mixture was further centrifuged for 15 min at 2800×g and the supernatant transferred to another tube. A second extraction was performed and the supernatants from each extraction were added together and were subjected to the Bradford assay using standard solutions of Bovine Serum Albumin (BioRad) with concentration ranges from 100 ug/ml to 1500 ug/ml. Total protein was quantified by absorbance measurements at 595 nm wavelength.

Example 8

Cell Rupture or Temporary Disruption

The ability to collect the lipid fraction of cells depends on the genus and species of algae. Further, either partial or complete cell disruption is required for extraction of cellular components.

The cell rupture process can be optimized in the presence of ionic liquids prior to fractionation. Different from hydrophilic solvents, the ability of ionic liquids to extract lipids depends on a second solvent system, such as variations on methanol-acetone-DMSO-isopropanol; however, no second solvent is required during cell rupture.

In addition, sonication can be used for cell rupture. To release specific cell contents, the rate and intensity of ultrasonication can be further varied to achieve, for example, temporary disruption for lipid removal, or otherwise complete cell destruction.

Electrical lysis, gas pressure rupture, or other physical methods may be necessary for algal slurry lysis. Some preparations may further require a heating step at a temperature of at least 55° C. for about 30 minutes.

In an embodiment, ionic liquids are added to the lyophilized algae samples and sonicated using a sonicator dismembrator. Sonication is performed at 45-47° C. for 10 minutes with 50% amplitude with the sample mixture under ice-bath during the whole sonication process.

Yet in another instance, the sonication process is performed on larger volumes of algae cultures using the same sonication parameters mentioned above to effect the same oil extraction process. Three liters of the algae cultures concentrated to a slurry or its lyophilized equivalent of 5 g is added with ionic liquid (IL) at a ratio of 1 g:45 mL IL in a beaker and stirred with magnetic stir bar for 1 minute. The large-volume mixture is allowed to flow into the sonicator dismembrator through a continuous flow attachment.

Example 9

Further Processing of Lipid Phase

The crude lipid extracted from biomass can be further processed as is known in the art for production of biofuels, industrial chemicals and chemical intermediates. Alternatively, the crude lipid can be processed by industrial biotransformations.

In one instance, the lipid phase can be treated by applying a hydrogenating catalyst to allow site-specific saturation of monounsaturated or other unsaturated hydrocarbons during the lipid separation phase. In another instance, the lipid phase is treated with an acid phase containing acetic acid, hydrogen peroxide, and peracetic acid in aqueous solution for epoxidation, as described in U.S. Pat. No. 4,647,678. In another instance, the saturated hydrocarbons are desaturated at central positions in their hydrocarbon chains by a desaturase enzyme, such as is present in mutant *Rhodococcus* spp.

In another instance, algae are engineered to express ricinoleic acids, including for example from the oleic acid present in abundance in some algae strains, or under certain conditions for induction of transgene expression. In yet another instance, inclusion of additional agents in the ionic liquid reaction medium allows enzymatic or other catalytic reactions to occur during the lipid separation phase.

Example 10

Separation of Lipids from IL-Lipid Extract and Recovery of IL

Separation steps are based on differential liquid densities, as is known in the field. In one instance, the IL-lipid extract is treated with an antisolvent to recover the ionic liquids as well as to isolate the pure crude lipids. To a fixed volume of the IL-lipid extract, an equivalent volume of an antisolvent is added. Such antisolvent includes any inorganic salt solution, for example, $CaCl_2$.

In one embodiment, antisolvent is added to the IL-lipid extract in a flask. The mixture is then vigorously stirred for at least 4 hours to allow formation of an initial biphasic system, whereby the ionic liquid is extracted by the salt solution. The whole biphasic system is subsequently transferred to a separatory funnel and allowed to settle until the initial biphasic system transforms to three separate and distinct layers: an lipid layer on the top, an IL-salt layer at the middle, and an aqueous layer at the bottom. All three layers are collected as is known in the art. Then, the middle layer is further separated into its components; the top layer is prepared as is known in the art, for qualitative analysis by thin layer chromatography, quantitative analysis by gas chromatography, or composition analysis by HPLC; and the bottom layer is further tested for IL residues.

In another instance, IL is recovered from the IL-salt complex by adding another solvent that dissolves only the salts, leaving the IL insoluble. For a fixed volume of IL-salt complex, an equivalent volume of deionized water or any compatible polar solvent is added. The mixture is further separated as is known in the art. The IL recovered by this technique can be reused subsequently.

Example 11

Rapid Assay of Lipid Content in Algae

Lipid-producing algae strains may be developed by screening and selecting potential algae strains based on the total lipid content. This process can be practiced using the extraction procedure as described in Example 6. First, the top layer lipid content is determined by fluorescence spectroscopy, using fluorochromes such as BODIPY, Primuline, Rhodamine B that are specific for lipids.

In one instance, the lipid-IL layer (top layer) is treated with BODIPY (20 mg/ml) in a ratio of 2:3 v/v. The preparation is intermittently vortexed every minute to allow thorough mixing and binding of the dye. The vortexed preparation is left to stand for 5 minutes to stabilize dye-lipid interaction. Then, fluorescence measurement is applied, using a spectrofluorimeter, with the appropriate excitation and emission filters. The total lipid content is calculated based on an established standard curve, for example using triolein. This can be obtained as is known in the art with concentrations ranging, for example, from 2 ug, 8 ug, 10 ug, 16 ug, and 20 ug.

Yet in another instance, the dye can be added during the extraction, as described in Example 6, to immediately bind lipids extracted by the IL. The extraction is then centrifuged to yield a lipid layer, which is further analyzed using fluorescence measurements. Such technique limits the whole process of extraction and fluorescence analysis to fewer steps, hence, allows a quicker process for complete analysis.

Example 12

Determination of Total Lipid Content of the Lipid-IL Extract from Algae

The ability of the IL to extract lipids from the algae is determined from the total lipid content present in the lipid-IL extract. The total lipids, separated by methods as described in Example 10, can be further analyzed for composition using the fluorescence measurements protocol as described in Example 11. For example, 1 L algae with cell density of $5.8 \times 10^8$ contains 0.1511 g of lipid (dry weight). Alternatively, 1.27 ml algae is needed to produce 20 ug total lipids in a 1:3 v/v ratio of IL:lipid mixture. For further lipid extraction, 423 uL of hydrophobic ionic liquid is added, and the mixture is sonicated, as is known in the art. The sonicated sample is further centrifuged, and the supernatant lipid-IL layer is removed from the biomass. A protocol is not yet available to directly quantify the total lipid content in the extracted oil-IL phase due to interference of IL with standard analytical methods. The percent total oil in the extract (percent oil recovery) can be measured indirectly by analyzing the percent total oil in the control (untreated) and in the IL-treated biomass. The difference in oil content between the control and treated samples is reported as the percentage oil recovery in the IL-oil phase. In one instance, the biomass obtained from oil extraction in Example 6 is lyophilized and analyzed by GC-MS for total oils (as FAMES) and compared to the total oils present in the untreated biomass.

In another instance, extent of IL extraction is determined qualitatively. The supernatant lipid-IL layer obtained from sonication in Example 6 is analyzed for presence of lipids using Nile Red assay as known the art. Qualitatively, high fluorescence reading is an indication of a significant amount of lipids bound by Nile Red dye and is directly proportional to lipid concentration.

The total lipid content is determined by treating the lipid layer with a lipid-specific fluorescent dye such as Nile Red, primulin or any other lipid-specific dye in the manner described above. In another instance, the lipid layer is prepared as is in known in the art, for qualitative analysis by thin layer chromatography, quantitative analysis by gas chromatography, or composition analysis by HPLC.

Example 13

Scale-Up for Recovery of Lipids from Lysed Algal Concentrate

Separation of lipids from lysate can be performed in the presence of a membrane interface, permissive of hydrophobic compound transfer in a counter-current operation. The ionic liquids can replace organic solvents such as hexane in one flow direction. Pumping action can easily accommodate ionic liquids with varying viscosities, such as from 3× to 20× that of water.

Example 14

Recovery of Lipids by Non-Destructive Extraction

Using methods of continuous extraction of lipids by brief ultrasonication, lipids can be removed without destruction of cells. Conventional alkane-based organic solvent blends used in the art are substituted with ionic liquids.

Example 15

Harvesting Algal Biomass by Chemical Dewatering

Chemical dewatering agents are agents that cause separation of algal cells from their culturing medium. Different modes of chemical dewatering occur depending on how the agents interact with the algal cells. Ionic liquids are lipophilic that can also act as chemical dewatering agent by extracting algal cells rich in lipid bodies into the IL layer. This causes a separation of the cells from the culture medium, a process called chemical dewatering. In an embodiment, ionic liquid is added in a ratio of 1:2 v/v to fresh algal cultures with cell density of $4 \times 10^8$ cells/ml or higher. The preparation is left to stand for ~20 hours to allow cells to interact with the ionic liquid and migrate into the IL layer and separate from the culturing medium. The dewatered cells from the IL layer are skimmed off from the top layer and further concentrated by gravity separation as known in the art.

We claim:

1. A method of extracting lipid from a microbial biomass that contains lipid, other hydrocarbon components, carbohydrates, and/or proteins, wherein the method comprises:
   (a) applying a hydrophobic ionic liquid solvent to the microbial biomass so that the lipid becomes at least partially dissolved in the hydrophobic ionic liquid solvent to form a lipid-solvent and microbial biomass mixture, wherein the mixture comprises a lipid-solvent layer;
   (b) separating at least part of the lipid-solvent layer from the mixture to obtain a lipid-solvent component and an at least partially delipidated component; and
   (c) recovering lipid from the lipid-solvent component by applying an antisolvent to the lipid-solvent component, thereby removing the hydrophobic ionic liquid from the lipid-solvent component, wherein the antisolvent is an inorganic salt solution immiscible with lipid.

2. The method, according to claim 1, further comprising disturbing the lipid-solvent and microbial biomass mixture formed according to step (a) to facilitate the formation of a lipid-solvent layer.

3. The method, according to claim 2, wherein the formation of the lipid-solvent layer in step (a) occurs at a temperature of less than 55° C. and at an ambient pressure.

4. The method, according to claim 1, wherein the microbial biomass comprises saturated lipids, and the lipid-solvent component comprises a saturated lipid.

5. The method, according to claim 4, wherein the saturated lipid comprises a fatty acid selected from the group consisting of C10, C12, C14, C15, C16, C17, C18, C19, C20, C22, and C24 fatty acid.

6. The method, according to claim 1, wherein the microbial biomass comprises unsaturated lipids, and the lipid-solvent component comprises an unsaturated lipid.

7. The method, according to claim 1, wherein the microbial biomass comprises polyunsaturated lipids, and the lipid-solvent component comprises a polyunsaturated lipid.

8. The method, according to claim 1, wherein the biomass is selected from the group consisting of yeast, cyanobacteria, archaea, and bacteria.

9. The method, according to claim 1, wherein the biomass is algae.

10. The method, according to claim 9, wherein the algae species is selected from the group consisting of *Amphora, Anabaena, Anikstrodesmis, Botryococcus, Chaetoceros, Chlorella, Chlorococcum, Cyclotella, Cylindrotheca, Euglena, Hematococcus, Isochrysis, Monodus, Monoraphidium, Nannochloris, Nannochloropsis, Navicula, Nephrochloris, Nephroselmis, Nitzschia, Nodularia, Nostoc, Oochromonas, Oocystis, Oscillartoria, Parachlorella, Pavlova, Phaeodactylum, Pinguiococcus, Playtomonas, Pleurochrysis, Porphyra, Pseudoanabaena, Pyramimonas, Rhodomonas, Scenedesmus, Selenastrum, Stichococcus, Synechococcus, Tetraselmis, Thalassiosira,* and *Trichodesmium.*

11. The method, according to claim 1, further comprising using the lipid-solvent component to produce biofuels.

12. The method, according to claim 1, wherein the at least partially delipidated component comprises a selectively delipidated component, and further comprising using the selectively delipidated component as a food source.

13. The method, according to claim 12, further comprising enriching the selectively delipidated component with at least an unsaturated lipid.

14. The method, according to claim 13, wherein the unsaturated lipid used for enriching the selectively delipidated component is selected from the group of fatty acids consisting of C18, C20, C22, omega-6, omega-3, omega-9, polyunsaturated fatty acid (PUPA), arachidonic acid (ARA), docosahexaenoic acid (DHA), eicosapentaenoic acid (EPA), and dihomo-gamma-linolenic acid (DGLA).

15. The method, according to claim 14, further comprising using the enriched selectively delipidated component as a part of a feed formulation.

16. The method, according to claim 1, further comprising separating the at least partially delipidated component into fractions comprising a protein fraction.

17. The method, according to claim 1, further comprising separating the at least partially delipidated component into fractions comprising a carbohydrate fraction.

18. The method, according to claim 1, further comprising combusting the at least partially delipidated component.

19. The method, according to claim 1, further comprising using the at least partially delipidated component in anaerobic digestion or fermentation.

20. The method, according to claim 1, wherein the hydrophobic ionic liquid solvent is non-toxic.

21. The method, according to claim 20, wherein the hydrophobic ionic liquid solvent is non-volatile.

22. The method, according to claim 1, wherein the hydrophobic ionic liquid is a protic hydrophobic ionic liquid.

23. The method, according to claim 22, wherein the protic hydrophobic ionic liquid is selected from the group consisting of hydronium ionic liquid, ammonium ionic liquid, alkylammonium ionic liquid, imidazolium ionic liquid, and heterocyclic ionic liquid.

24. The method, according to claim 1, further comprising the step of recovering the hydrophobic ionic liquid removed from the lipid-solvent component using an excess of water or any compatible polar solvent.

25. The method, according to claim 1, further comprising processing the remaining lipid fraction by chemical conversion.

26. The method, according to claim 1, further comprising determining lipid composition of the recovered lipid.

27. The method, according to claim 26, further comprising the step of determining the dry weight of each type of lipid of the recovered lipid.

28. The method, according to claim 26, wherein the biomass is selected from the group consisting of yeast, cyanobacteria, archaea, bacteria, and algae.

29. The method, according to claim 1, wherein the biomass is lysed before applying step (a).

30. The method, according to claim 29, wherein the ionic hydrophobic liquid is applied to the biomass in countercurrent flow.

* * * * *

UNITED STATES PATENT AND TRADEMARK OFFICE
CERTIFICATE OF CORRECTION

PATENT NO.         : 8,748,161 B2
APPLICATION NO.    : 12/954141
DATED              : June 10, 2014
INVENTOR(S)        : Kuehnle et al.

Page 1 of 1

It is certified that error appears in the above-identified patent and that said Letters Patent is hereby corrected as shown below:

In the specification,

Column 4,
Line 6, "Crypthccodinium" should read --Crypthecodinium--.
Line 37, "carbonhydrates" should read --carbohydrates--.
Line 66, "soluabilization" should read --solubilization--.

Column 7,
Line 22, "Tetrasclmis" should read --Tetraselmis--.

Column 8,
Line 2, "Chlorclla" should read --Chlorella--.
Lines 32-33, "Nitzschia lacvis" should read --Nitzschia laevis--.

Column 11,
Line 19, "thiamine.HCl" should read --thiamine • HCl--.
Line 22, "$MnCl_2.H_2O...CuSO_4.5H_2O$" should read --$MnCl_2 \cdot H_2O...CuSO_4 \cdot 5H_2O$--.

Column 14,
Lines 52-53, "layers: an lipid layer" should read --layers: a lipid layer--.

Signed and Sealed this
Fourteenth Day of April, 2015

Michelle K. Lee
*Director of the United States Patent and Trademark Office*